(12) United States Patent
Hart et al.

(10) Patent No.: US 7,093,949 B2
(45) Date of Patent: Aug. 22, 2006

(54) IMITATION FLAME AIR FRESHENER

(75) Inventors: Gerald Leslie Hart, deceased, late of Surbiton (GB); by Susan Hart, legal representative, Surbiton (GB); Colin William Brown, Egham (GB); Guy Edward Naish, Bicester (GB); Kishen Gohil, New Malden (GB); Simone Anderson, Ashford (GB)

(73) Assignee: Givaudan SA, Dubendorf (CH)

( * ) Notice: Subject to any disclaimer, the term of this patent is extended or adjusted under 35 U.S.C. 154(b) by 0 days.

(21) Appl. No.: 10/766,425

(22) Filed: Jan. 27, 2004

(65) Prior Publication Data

US 2004/0257798 A1    Dec. 23, 2004

Related U.S. Application Data

(60) Provisional application No. 60/443,486, filed on Jan. 29, 2003.

(51) Int. Cl.
*F21V 33/00*    (2006.01)

(52) U.S. Cl. ............... 362/96; 362/253; 362/810; 422/125; 422/124; 40/428

(58) Field of Classification Search ............... 362/96, 362/101, 806, 92, 810, 253, 392; 422/1, 422/5, 120, 125, 124; 40/428; 472/65; 392/348
See application file for complete search history.

(56) References Cited

U.S. PATENT DOCUMENTS

| | | | | |
|---|---|---|---|---|
| 3,948,445 A | * | 4/1976 | Andeweg | 239/53 |
| 5,498,397 A | * | 3/1996 | Horng | 422/124 |
| 5,967,639 A | * | 10/1999 | Shih | 362/101 |
| 6,454,425 B1 | * | 9/2002 | Lin | 362/96 |
| 2003/0007887 A1 | * | 1/2003 | Roumpos et al. | 422/1 |
| 2004/0264169 A1 | * | 12/2004 | Limburg et al. | 362/96 |

* cited by examiner

*Primary Examiner*—Thomas M. Sember
(74) *Attorney, Agent, or Firm*—Norris McLaughlin & Marcus PA

(57) ABSTRACT

A device is described which includes a vertical body, the vertical body having contained therein a wick and a source of a vaporizable material. The vertical body further includes at an open end a silky material with irregular shapes to simulate the profiles of a flame such as a candle flame. Within the vertical body is a means for supplying an air current such that, when operating, the air current passes upward causing the silky material to flutter and simulate a flame, while also entraining vaporizable material which is present in the wick.

12 Claims, 2 Drawing Sheets

IMITATION FLAME AIR FRESHENER

This application claims the benefit of Provisional Application No. 60/443,486, filed Jan. 29, 2003.

The present invention generally relates to devices used to deliver a volatile substance into an ambient environment, such as a fragrance, odor masking agent or the like.

Recently, air freshening and air fragrancing candles have returned to popularity amongst the public. Such devices are popular and effective in that the lighted candle flame is attractive and visually pleasing to the observer, while the same time and the heated pool of fuel (typically a paraffin, or microcrystalline wax) near the flame operates as a satisfactory reservoir for a fragrancing or odor masking substance. Such fragrancing or odor masking substances are typically volatile materials which, when heated to the melt temperature of the fuel emanate from candles in into the ambient environment. However, although attractive these are also inherently dangerous devices in that one left unattended may be the cause of personal harm to consumers, or the source of a fire hazard.

Devices which simulate the appearance of open flames are known. For example, U.S. Pat. No. 4,965,707 describes a simulated flame effect means, such as suspended ribbons moved by a forced stream of air from a fan, receive light from a source which is then reflected onto a diffusing screen. The screen, which is both transparent and partly reflective, is situated in front of means for simulating combusting fuel. The light reflected by the flame effect means, which gives the appearance of flames, thereby appears to emanate between the simulated fuel and its image reflected in the screen. Such a device provides pleasing effect and is very well suited for simulation of a fireplace.

U.S. Pat. No. 3,603,013 describes an electronic illumination device particularly useful for use in a fireplace which includes a translucent viewing screen, an imitation fuel, and a suspended flexible material which is disposed inwards of the viewing screen, as well as a light source. Further provided is a means for causing airflow for moving the flexible material so to vary the lighting effect imported by the device. The airflow causes a random a flickering effect which is perceived as a flame effect through the viewing screen.

However such simulated flame devices appear to be generally limited to providing a visual effect, particularly when such devices are used to construct fireplace inserts replacing the traditional hearth and its burning logs.

The present invention provides the benefits of fan-driven fragrance release and flame imitation to provide a decorative air freshener that simulates a candle while providing a pleasant fragrance with no heat or naked flame, such as is a characteristic of candles. The benefit of such a design are that there are no safety issues with flammability of the device and further, there no restrictions on the fragrance ingredients that can be used in such a device as the chemical compatibility of the volatile air treatment material with the candle's fuel (paraffin wax, microcrystalline wax) ceases to be a consideration, and the effects of heat upon the volatile air treatment material also ceases to be a consideration as the mechanism of volatilization is not based on heat.

Figure 1:
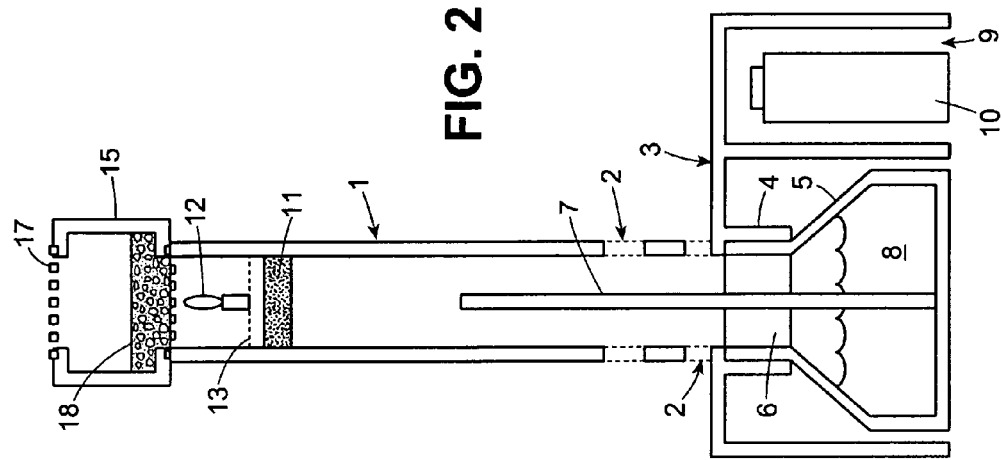
FIG. 1 depicts in cross sectional view the main elements of a first embodiment of the invention.

In one aspect the present invention provides an imitation flame air freshener device which comprises: an imitation flame, a fan, and a supply of volatile air treatment material.

In a further aspect of the present invention there is provided a method for dispensing a volatile air treatment material to the ambient environment which contemplates the steps of providing: an imitation flame air freshener device which comprises: an imitation flame, a fan, and a supply of volatile air treatment material.

and thereafter operating the said device in order to dispense the volatile air treatment material to the ambient environment.

Broadly, the present invention provides an imitation flame air freshener device which comprises: an imitation flame, a fan, and a supply of a volatile air treatment material, as well as a method of for dispensing the volatile air treatment material to the ambient environment such as to the interior of a room, vehicle, or other space in need of air treatment.

The imitation flame according to the present invention can be according to those of the type presently known in the art, particularly as those described in one or more of the prior patents. In one particular form, imitation flame is in the form of a thin flexible sheet of the material such as silk, or other fine material which can be cut into or otherwise formed into the shape of a flame. Such an imitation flame operates in that it is attached at one end, side or portion thereof to a rigid support such as a wire, post, frame, etc. and within an flowing current of air. Such a flowing current of air can be provided by any suitable means such as by differentials in air pressure, bursts of air, but most conveniently is provided by a fan such as a in electrical fan. The flowing current of air directed past the imitation flame causes it to flutter and to exhibit a kinetic appearance. Frequently also a small electrical light source such as a small lamp or an LED is provided within the proximity of the imitation flame and to illuminate its while it is fluttering; such provides a very realistic appearance to the imitation flame.

An alternative imitation flame according to the present invention is also provided by a small chamber which includes a plurality of finely divided particles, usually reflective particles such as comminuted foil, metallic glitter, are or other reflective particles. This chamber is frequently provided with a fine mesh or series of vent holes which is sufficient to retain in the finely divided particles within the confines of the chamber through which a flow of air is directed. Frequently, two find meshes or series of vent holes are provided on opposite sides of the chamber, which is most desirably transparent or translucent, to contain the finely divided particles within a flowing current of air passes into or through the chamber, thus animating the finely divided particles. When such chamber is utilized, it is often also utilized with a small lamp or an LED to illuminate the finely divided particles. In operation, the finely divided particles provided very attractive effect. As described above with reference to be imitation flame, the airflow can be provided by any suitable means, especially by the use of a small electrical fan.

The fan according to the present invention may indeed be any type of fan which is found effective to animate the imitation flame (or chamber) as discussed above, preferred embodiments of which are depicted within the examples. Desirably, the fan is small, and a suitable for operation from a power source particularly from a battery providing D. C. current, which battery is frequently suitably dimension to fit within the device in itself, thus concealing it from the consumers. Of course, other means for providing an a flowing current of air can be utilized although not described particularly herein.

The volatile air treatment material according to the invention can be any composition of matter, usually a liquid composition of matter which volatilizes in the operating environment of the imitation flame air freshener device. Such are frequently liquid compositions which may be used to provide a fragrancing, so-called air freshening, odor masking, insect controlling or one or more of these, as well as other effects. Such may be in the form of pure oils, such as pure essential oils but more commonly are in the form of mixtures of one or more constituents including water, such as to form aqueous compositions as well as blends or mixtures of various volatile materials absent any further materials, or with an aqueous base, or with an organic base, or with an aqueous and organic base. It is to be understood that such fragrancing, air freshening, odor masking, insect controlling or other such material can be relatively simple in composition, or can be a complex mixture of natural and synthetic chemical components, and any material which may be volatilized and dispensed by the use of the present invention may find use therewith. Fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like. Additionally a wide variety of chemicals are known for fragrancing, air freshening, odor masking, insect controlling or other effect such as aldehydes, ketones, esters, alcohols, terpenes, and the like. A typical scented oil can comprise woody/earthy bases containing exotic constituents such as sandalwood oil, civet, patchouli oil, and the like. A scented oil can have a light floral fragrance, such as rose extract or violet extract. Scented oil also can be formulated to provide desirable fruity odors, such as lime, lemon or orange. Synthetic types of fragrance compositions either alone or in combination with natural oils may also be used. Such synthetic liquid fragrance compositions include, inter alia, geraniol, geranyl acetate, eugenol, isoeugenol, linalool, linalyl acetate, phenethyl alcohol, methyl ethyl ketone, methylionone, isobornyl acetate, and the like. Other materials useful in fragrancing, air freshening and odor masking may also be used in the present invention, although not particularly elucidated herein. As noted above, the volatile air treatment material according to the invention may also be a formulation, such as a liquid formulation containing an insect repellent material, such as citronellal. Additionally the volatile air treatment material according to the invention may also be a formulation directed to provide a beneficial therapeutic effect, such as eucalyptus or menthol.

The air treatment material, when in a liquid form, is advantageously supplied within a vessel or bottle from which extends a porous body, e.g., a wick, which permits for the transfer of the air treatment material from within the vessel and to the exposed surface(s) of the wick extending from within the vessel, from which the air treatment material volatilizes. Preferably the vessel, bottle and wick are dimensioned to fit within the interior of the devices described herein so that they are obscured from view by a consumer during the normal operation of the device.

FIG. 1 shows the main elements of a first embodiment of the invention. Therein there is disclosed a tube 1 with vent holes 2 at its lowest portion, that is distal to the imitation flame. The tube 1 may be designed to resemble a candle if desired, as is depicted in FIG. 1. The tube is attached to a base unit 3 which has an internal collar 4 which can receive a refill bottle 5 (either by a screw thread or snap mechanism). The refill bottle 5 contains a neck insert 6 supporting a wick 7 which may be composed of any suitable porous material such as synthetic fiber, natural fiber (e.g. cellulose) or porous plastic. The refill bottle 5 contains as the supply of volatile air treatment material., a volatile liquid 8 which may, inter alia, be fragrance or insecticide as pure oil, as solution in water or as solution in organic solvent. The base unit 3 also houses a separate compartment 9 containing the battery 10. Alternatively, the device may be operated by mains power through a power transformer (not shown). Inserted towards the upper portion of the tube 1 is a fan 11 mounted in such a way that it draws air through the vent holes 2 and up the inside of the tube 1. Directly above the fan 11 is mounted a light bulb or LED 12 on a support 13 that does not impair the upward air flow. Directly above this is the imitation flame, here formed by a piece of thin fabric shaped and colored appropriately to resemble a flame 14. In operation, air is drawn through the vent holes 2, past the wick 7 where volatile material is evaporated, up the tube 1 and past the fabric flame 14 which is moved in the air stream in such a way as to imitate a real flame. The illumination from the light 12 completes the effect. It is envisaged that there is wiring running up the inside of the tube from the battery to the fan and light bulb, though this is not depicted in FIG. 1. It is also envisaged that there could be an on/off switch and optional timer or sensor to control the activation of the device, although now shown in the figure.

Figure 2:
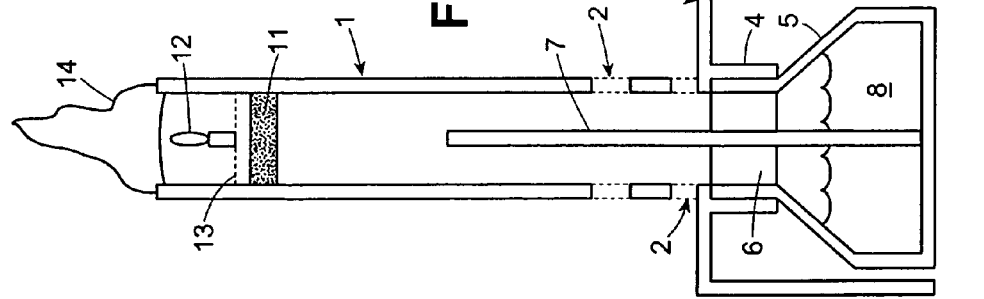
FIG. 2 illustrates a second embodiment of an imitation flame air freshener according to the invention.

FIG. 2 shows a further embodiment of the invention which is in many respects similar to the embodiment of FIG. 1, but in which the imitation flame is a chamber 15 composed of clear glass or plastic. This chamber has a mesh at its lower portion 16 and a corresponding mesh at its upper portion 17. The chamber is partly filled with small particles of colored material 18, such as paper, plastic chips or foil particles. The meshes 16 and 17 have an aperture size smaller than the smallest particle such that they are contained within the chamber 15. This embodiment illustrates that the silk flame (of FIG. 1) could be replaced with a chamber 15 filled with glitter or some other reflective and finely divided material. The upper and lower portions of this chamber would be covered with a fine mesh of sufficiently small aperture to contain the glitter while allowing the airflow from the fan to pass through. This chamber could be shaped like a flame such that while operating it would be filled with a swirl of glitter particles making up the shape of a flame.

Figure 3:
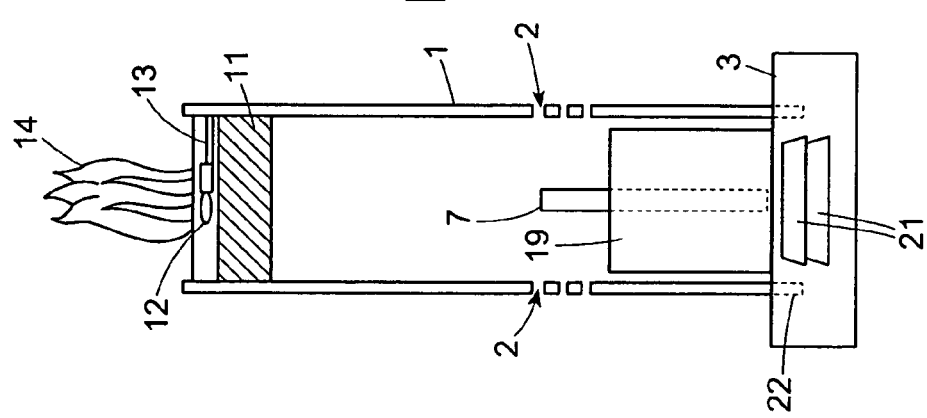
FIG. 3 shows a third embodiment of an imitation flame air freshener according to the invention.

FIG. 3 illustrates a further aspect of the invention. Herein is provided a tube 1 with vent holes 2 at its lowest portion, that is distal to the imitation flame. The tube 1 may be designed to resemble a candle if desired, as depicted. 1. The tube is attached to a base unit 3 which by a circular recess 22 which is dimensioned to received the tube 1. The refill bottle 19 supporting a wick 7 is inserted above the base 3, and within the interior of the tube 1. This refill bottle 19 contains as the supply of volatile air treatment material, a volatile liquid 8 which may, inter alia, be fragrance or insecticide as pure oil, as solution in water or as solution in organic solvent as described previously. The base unit 3 also houses one or more batteries 21, here coin cells which are generally circular and plate like in their design; such coin cells permit for a low profile base 3 to be constructed. Alternatively, as described with reference to FIG. 1 the device may be operated by mains power through a power transformer (not shown).

Positioned towards the upper portion of the tube 1 is a fan 11 mounted in such a way that it draws air through the vent holes 2 and up the inside of the tube 1. Directly above the fan 11 is mounted a light bulb or LED 12 on a support 13 that does not unduly impair the upward air flow. Directly above this is the imitation flame, here formed by a piece of thin fabric shaped and colored appropriately to resemble a flame 14. In operation, air is drawn through the vent holes 2, past the wick 7 where volatile material is evaporated, up the tube 1 and past the fabric flame 14 which is moved in the air stream in such a way as to imitate a real flame. The illumination from the light 12 completes the effect. It is envisaged that there is wiring running up the inside of the tube from the batteries to the fan and light bulb, though this detail is not depicted in FIG. 1. It is also envisaged that there could be an on/off switch and optional timer or sensor to control the activation of the device, although now shown in the figure.

Figure 4:
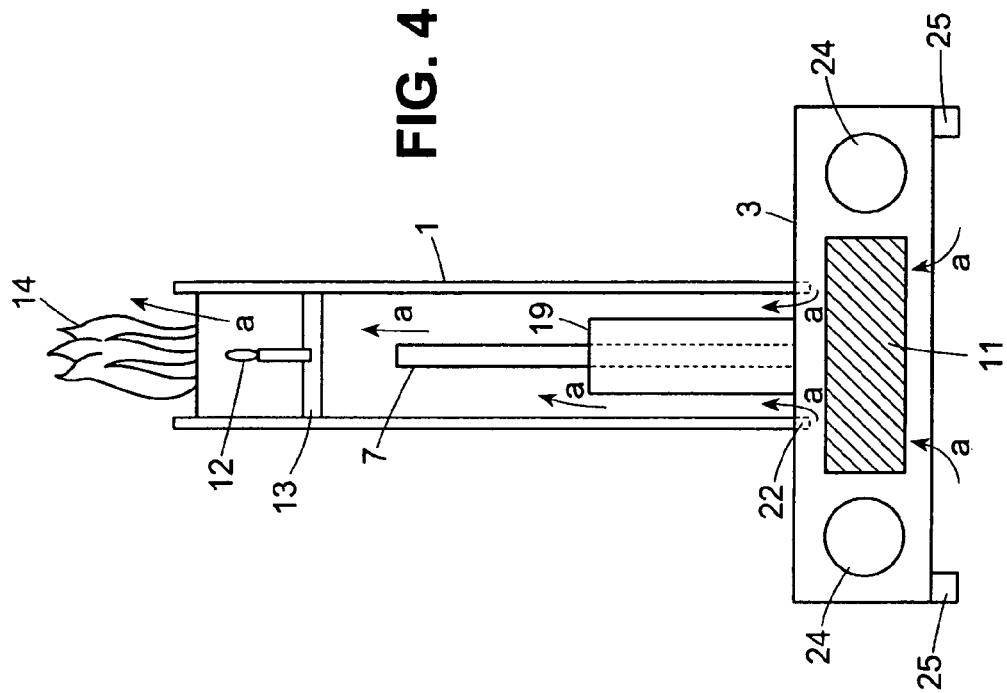
FIG. 4 depicts a fourth embodiment of an imitation flame air freshener according to the invention.

FIG. 4 depicts a yet further aspect of the invention, here with a fan in the base of the device. Therein is provided a tube 1 with vent holes 2 at its lowest portion, that is distal to the imitation flame 14. The tube 1 may be designed to resemble a candle if desired, as depicted. 1. The tube is attached to a base unit 3 by a circular recess 22 which is dimensioned to received the tube 1. The refill bottle 19 supporting a wick 7 is inserted above the base 3, and within the interior of the tube 1. This refill bottle 19 contains as the supply of volatile air treatment material, a volatile liquid 8 which may, inter alia, be fragrance or insecticide as pure oil, as solution in water or as solution in organic solvent as described previously. The base unit 3 also houses one or more batteries 21, here generally circular cells, here intended to depict "AA" sized batteries in a cross-sectional view. Alternatively, as described with reference to FIG. 1 the device may be operated by mains power through a power transformer (not shown).

Positioned with the base 3 is provided a fan 11 mounted in such a way that it draws air from within the base, here via vent holes (not visible) on the underside of the base 3, and direct the airflow (arrows "a") up and into the inside of the tube 1.

Near the top of the tube 1 there is mounted a light bulb or LED 12 on a support 13 that does not unduly impair the upward air flow. Directly above this is the imitation flame, here formed by a piece of thin fabric shaped and colored appropriately to resemble a flame 14. In operation, air is drawn through the base 3 and upwards into the tube 1, and past the wick 7 where volatile material is evaporated, and past the imitation flame 14 which is moved in the air stream in such a way as to imitate a real flame. The illumination from the light 12 completes the effect. It is envisaged that there is wiring running up the inside of the tube from the batteries to the fan and light bulb, though this detail is not depicted in FIG. 1. It is also envisaged that there could be an on/off switch and optional timer or sensor to control the activation of the device, although now shown in the figure.

It is to be understood that in addition to, or as alternative to the battery power, or mains power described herein it is contemplated also that the electrical power used to drive the fan may be any power source, including AC supply via a suitable transformer, from a rechargeable battery, or for that matter via solar cells, as well as any combination thereof. Further, it is also to be understood that the imitation flame 14 shown in FIG. 1, 2 or 4 may be substituted by the imitation flame 14 according to FIG. 2.

The invention claimed is:

1. An imitation flame air freshener device which comprises:
    a supply of volatile air treatment material; a fan;
    an imitation flame being positioned such that it lies in the path of a flowing current of air emitted from said fan and which transports the volatile air treatment material said imitation flame being selected from (i) a thin flexible sheet and (ii) a chamber containing a plurality of finely-divided particles.

2. A device according to claim 1 which further comprises:
    an electrical light source within the proximity of the imitation flame.

3. An imitation flame air freshener device according to claim 1 wherein said device comprises (ii) a chamber containing a plurality of finely-divided particles, said chamber which further comprises a fine mesh or series of vent holes adapted to permit the a flowing current of air into the chamber.

4. An imitation flame air freshener device according to claim 3 wherein the finely divided particles are selected from comminuted foil, metallic glitter, are or other reflective particles.

5. A device according to claim 3 which further comprises:
    an electrical light source within the proximity of the chamber.

6. A device according to claim 1 wherein the fan is a fan operable from a battery providing DC current.

7. A device according to claim 1 wherein the volatile air treatment material is a fragrancing composition.

8. A device according to claim 1 wherein the volatile air treatment material is an air freshening composition.

9. A device according to claim 1 wherein the volatile air treatment material is an insect controlling composition.

10. A method for dispensing a volatile air treatment material to the ambient environment which contemplates the steps of:
    providing an imitation flame air freshener device according to claim 1; and,
    thereafter operating the said device in order to dispense the to the ambient environment.

11. The method according to claim 10 wherein the ambient environment is the interior of a room.

12. The method according to claim 11 wherein the ambient environment is the interior of a vehicle.

* * * * *

UNITED STATES PATENT AND TRADEMARK OFFICE
CERTIFICATE OF CORRECTION

| | |
|---|---|
| PATENT NO. | : 7,093,949 B2 |
| APPLICATION NO. | : 10/766425 |
| DATED | : August 22, 2006 |
| INVENTOR(S) | : Hart et al. |

It is certified that error appears in the above-identified patent and that said Letters Patent is hereby corrected as shown below:

Column 6, Lines 29-32, "An imitation flame air freshener device according to claim 3 wherein the finely divided particles are selected from comminuted foil, metallic glitter, are or other reflective particles." should read -- An imitation flame air freshener device according to claim 3 wherein the finely divided particles are selected from comminuted foil, metallic glitter, or other reflective particles. --

Signed and Sealed this

Eighteenth Day of November, 2008

JON W. DUDAS
*Director of the United States Patent and Trademark Office*